United States Patent [19]
Hellmuth et al.

[11] Patent Number: 5,607,652
[45] Date of Patent: Mar. 4, 1997

[54] BIOLOGICAL AND CHEMICAL DECONTAMINATION CHAMBER

[75] Inventors: Paul Hellmuth, Niederfell; Norbert Klein, Fassberg; Michael Theis, Emmelshausen, all of Germany

[73] Assignee: Dornier GmbH, Germany

[21] Appl. No.: 323,685

[22] Filed: Oct. 17, 1994

[30] Foreign Application Priority Data

Oct. 15, 1993 [DE] Germany ............ 43 35 233.5

[51] Int. Cl.⁶ .................... A61L 2/06; B08B 3/00
[52] U.S. Cl. ............ 422/300; 422/26; 422/304; 422/900; 34/203; 134/82
[58] Field of Search .............. 422/26, 300, 304, 422/307, 308, 900, 297; 34/203, 208, 216, 217; 134/82, 83

[56] References Cited

U.S. PATENT DOCUMENTS

| | | | |
|---|---|---|---|
| 4,490,924 | 1/1985 | Lambert | 34/216 |
| 4,597,192 | 7/1986 | Sfondrini et al. | 34/216 X |
| 4,655,235 | 4/1987 | Scott, Jr. | 422/119 X |
| 4,773,321 | 9/1988 | Wijts | 422/304 X |
| 4,850,380 | 7/1989 | Koslow | 134/56 R |

FOREIGN PATENT DOCUMENTS

| | | |
|---|---|---|
| 0138688 | 4/1985 | European Pat. Off. |
| 3119664 | 12/1982 | Germany |
| 3421719 | 12/1985 | Germany |
| 4335233 | 9/1994 | Germany |
| WO83/02243 | 7/1983 | WIPO |

OTHER PUBLICATIONS

Patent Abstract of Japan, JP3001029, dated May 26, 1989.
Patent Abstract of Japan, JP2017067, dated Jul. 2, 1988.

*Primary Examiner*—Robert J. Warden
*Assistant Examiner*—E. Leigh Dawson
*Attorney, Agent, or Firm*—Evenson, McKeown, Edwards & Lenahan P.L.L.C.

[57] ABSTRACT

The invention provides a transportable reaction chamber for continuous biological and chemical decontamination of articles by means of a mixture of hot air and steam. The reaction chamber has a tunnel shaped reaction section through which the contaminated articles are transported on a conveyor and through which a mixture of decontaminant gases is circulated. An exhaust blower situated at an end of the reaction section, and transverse flow units along its length, provide both transverse and longitudinal gas flow in the reaction section.

11 Claims, 3 Drawing Sheets

BIOLOGICAL AND CHEMICAL DECONTAMINATION CHAMBER

BACKGROUND AND SUMMARY OF THE INVENTION

The invention relates to a reaction chamber, arranged lengthwise and mountable on a chassis, for continuous biological and/or chemical decontamination of objects using a mixture of at least hot air and steam.

German Patent Document DE-PS 34 31 719 teaches such a reaction chamber of this generic type in which, instead of baskets for receiving any type of object, specially designed clothes hangers to receive protective clothing are used. These hangers are hollow inside and have through holes, so that a gas mixture supplied to the clothes hangers from above through a pressure tube flows out of the holes, ventilating the interior of the clothing. Depending on the position of the hangers on the conveyor tracks, such internal ventilation alternates with external ventilation. In both cases, the spent gas mixture is drawn off again immediately below the clothes hangers, is cleaned, and fed back again to the hot gas generator, resulting in a circulatory process. A plurality of reaction sections are arranged side by side along the length of the reaction chamber, to achieve parallel operation. No spatial separation is provided between the individual reaction sections.

The above described reaction chamber has the disadvantage that alternate internal and external ventilation of protective suits is complicated and costly. Since nearly the entire hot gas mixture is transported in a cycle, its preparation and cleaning are costly. Moreover, as far as the degree of contamination is concerned it is also disadvantageous that the reaction sections located side by side are not separated from one another, and that no clear separation is provided between the unclean and clean parts of the decontamination sections.

Because of the hanger construction that serves to receive articles of clothing and to ventilate them internally, decontamination is intended primarily for detoxification of protective suits.

A reaction chamber with a transverse blower is disclosed in German Patent Document DE-PS 36 25 847, in which the hot gas mixture is recirculated in the reaction chamber. In this known device, however, batched decontamination is performed, with the articles of clothing retaining their places in the reaction chamber during decontamination, a process that is completely the opposite of continuous decontamination.

The goal of the present invention is to provide a gas supply and gas exhaust system for a reaction chamber of a mobile device for continuous decontamination of objects using a mixture of at least hot air and steam, in which the nature of the objects decontaminated is variable, and which is simple, economical, and efficient, in terms of the biological and chemical decontamination to be performed.

This and other objects and advantages are achieved by the decontamination chamber according to the invention, in which the reaction section is made in the form of a tunnel, and is enclosed all the way around in cross section. This arrangement produces a clear separation between unclean and clean areas, so that a high level of decontamination and efficiency is achieved in conjunction with a powerful transverse flow of gases. A conveyor guide rail defines a track or path through the decontamination section, along which are transported a plurality of baskets into which articles to be decontaminated are placed. The transverse flow of hot gases penetrates the articles in the baskets and is drawn off by a longitudinal flow generated by a blower at an end of the reaction section. Regardless of the nature of the articles to be decontaminated, the transverse flow provides ventilation, and hence good heat transfer to the articles, which is critical for biological and chemical decontamination.

The advantages achieved with the invention consist in the fact that the hot gas mixture generated by the gas generator acts in simple fashion on the baskets moved along a guide. The gas mixture is initially conducted through the reaction sections, then drawn off and exhausted into the open. Because it is exhausted into the open, no costly preparation of the gas flow is required as in the known device. The baskets are also subjected to a powerful transverse flow in which the hot gas mixture is circulated transversely with respect to the lengthwise flow.

Other objects, advantages and novel features of the present invention will become apparent from the following detailed description of the invention when considered in conjunction with the accompanying drawings.

DETAILED DESCRIPTION OF THE PREFERRED EMBODIMENTS

Figure 1:
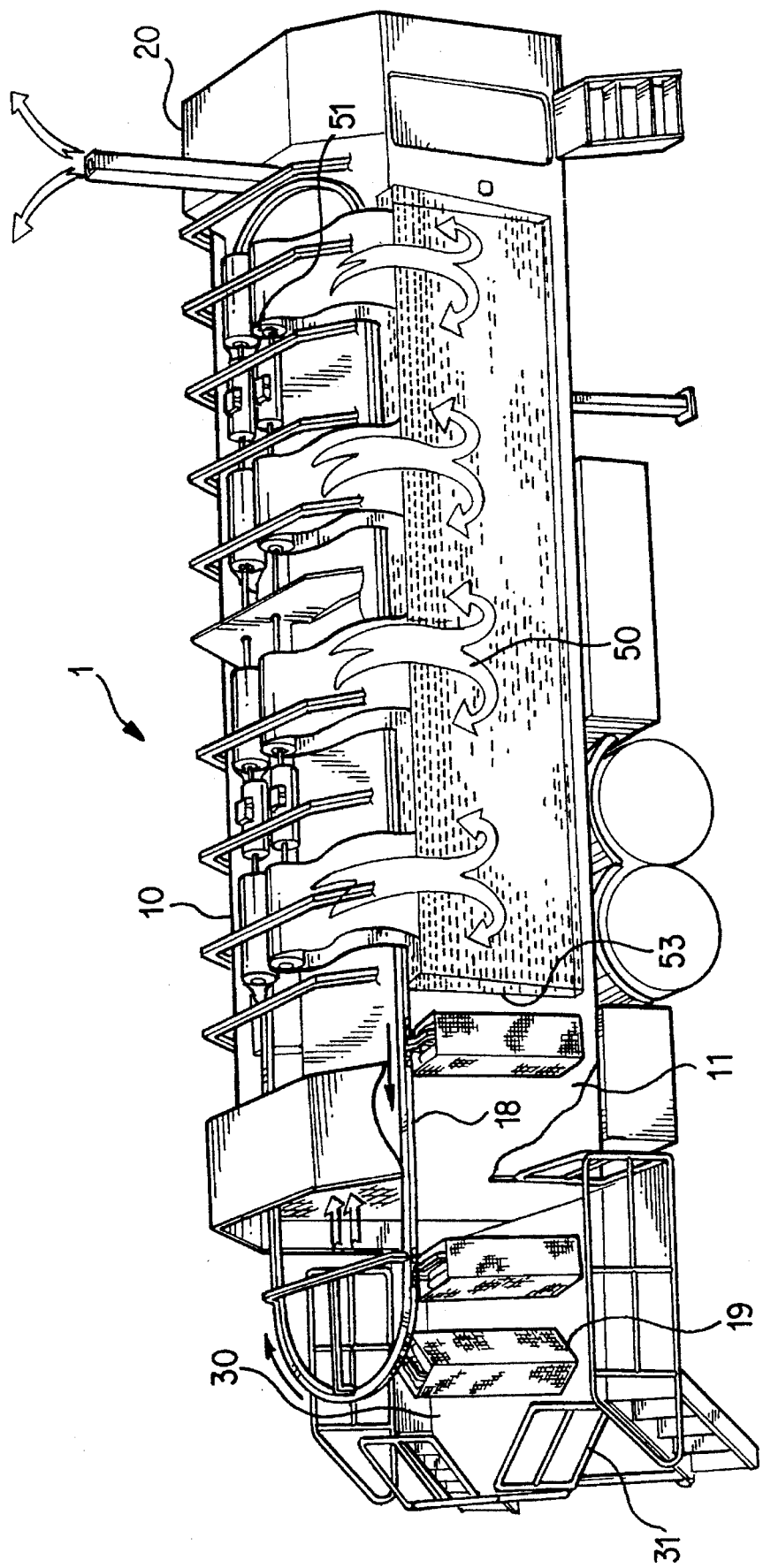
FIG. 1 shows a transportable reaction chamber, for continuous biological and/or chemical decontamination of articles of clothing and/or equipment according to the invention, in a perspective and partially cut-away view.

FIG. 1 shows a trailer 1 in which a device for continuous decontamination of articles of clothing and/or equipment is built on a chassis. This embodiment is designed to decontaminate 62 sets of clothing and equipment per hour, although it is apparent that other designs, with other throughput capacities, can be utilized within the scope of the invention. The length of the trailer including the tractor is 16.5 m, its width is 2.48 m and its height 3.74 m, so that commercial tractor-trailers suitable for use on the public roads may be used.

The device for decontamination is divided into an equipment room 20, a reaction chamber 10, and a loading and unloading station 30.

Figure 3:
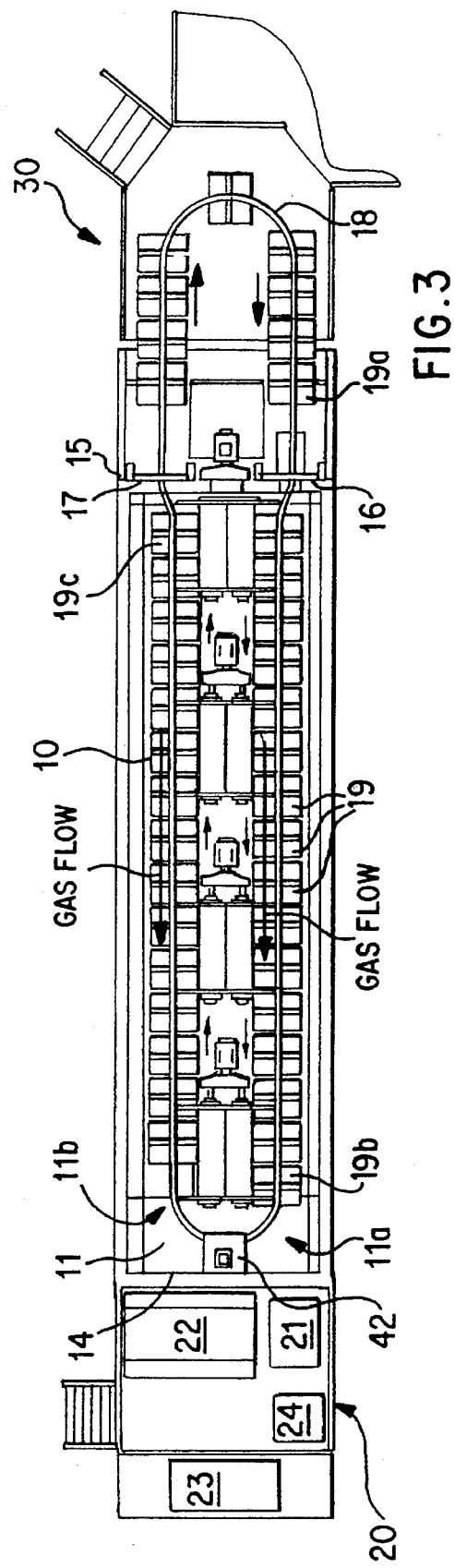
FIG. 3 is a top view of the trailer shown in FIG. 1, in section.

Equipment room 20 (FIG. 3) comprises a supply tank 22 for water (for example, 800 liters) and a supply tank 21 (for example, 200 liters) to permit independent operation for a period of about 3 hours, a complete electrical system with an externally mounted motorgenerator set (for example, 6.5 kVA) 23, and a control system (SPS) 24, which determines the operating mode and operates the system.

Reaction chamber 10 (FIG. 3) comprises a tunnel-shaped reaction section 11, a conveyor system for gaspermeable baskets 19, containing the contaminated objects, a gas supply and gas exhaust system for the hot gas mixture for biological and chemical decontamination, and spray heads for applying a decontamination solution and for washing it off, for nuclear decontamination.

The loading and unloading station 30 (FIG. 2) comprises a working platform 31, a hot gas generator 32, and heaters.

As shown in FIG. 1, the entire device can be operated with the trailer 1 uncoupled. After setup, with working platform 31 and the conveyor system for baskets 19 in place as shown, the operating mode is selected by the SPS control. A choice can be made between biological and chemical or nuclear decontamination, as described hereinafter. While biological and chemical decontamination is performed with a hot gas mixture, nuclear decontamination uses liquids.

Figure 4:
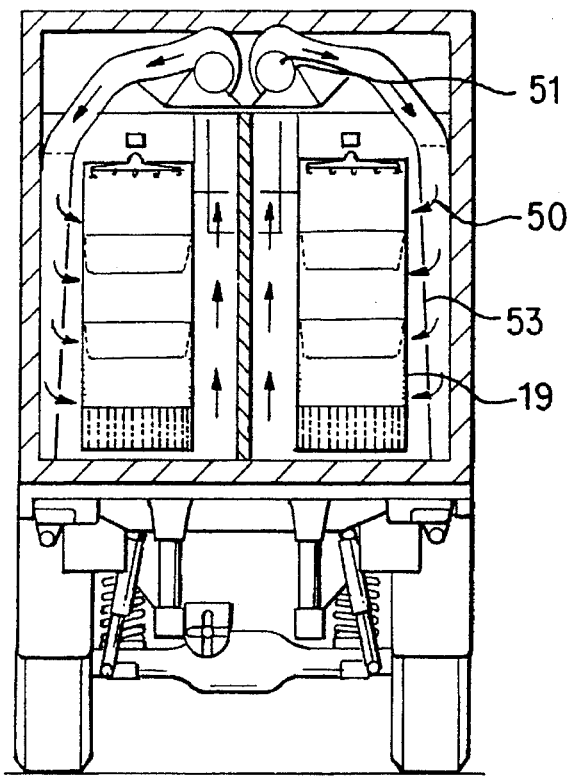
FIG. 4 is a side view of the trailer shown in FIG. 1, in section.

Two persons are required for decontamination operation of the complete unit, with their main tasks being loading baskets 19 with the contaminated objects and unloading the decontaminated material. Baskets 19 (FIGS. 1, 2 and 4) are 1.5 m high, 0.5 m wide, and 0.6 m deep, to hold the complete clothing and equipment of a soldier or a civil defense worker, corresponding to a total volume of approximately 0.5 m$^3$ and a total weight of about 40 kg.

The details of the device will first be described with respect to biological and chemical decontamination. Before actual operation begins, the entire system is brought to operating temperature using hot steam generator 32 (FIG. 2) and two additional heaters (not shown). Experiments have shown that the ideal decontamination temperature is 170° C., at which chemical contaminants and weapons or poisons are decomposed into harmless substances and biological contaminants and weapons are destroyed. In the case of objects that are sensitive to temperature, the temperature can also be reduced to 130° C. The decontamination mixture may consists, for example, of 50% waste gases from a diesel oil burner and 50% steam. Other combinations and percentage mixtures of decontaminant gases may of course be used within the scope of the invention.

The reaction section 11 (FIG. 3) is shaped like a tunnel and enclosed all the way around in cross section. It has tracks 18 and is composed of two partial segments 11a and 11b located side by side, running in the lengthwise direction of reaction chamber 10.

The first and second partial segments 11a and 11b of reaction section 11 are arranged side by side, and in the shape of an arc at the front end 14 of reaction chamber 10. At the rear end 15, in other words at the opposite end of reaction section 11, entrance and exit doors 16 and 17 are provided. A guide rail 18 of the conveyor system runs through the reaction section, along which rail gas-permeable baskets 19 can be moved. In the vicinity of loading and unloading station 30, guide rail 18 is in the shape of an arc. Individual baskets 19 always remain engaged with enclosed guide rail 18 (FIGS. 1 and 3) and are moved continuously in a circular fashion past individual stations, which include loading items into the baskets 19 at the loading and unloading station 30, decontamination in reaction chamber 10, and unloading of the baskets at loading and unloading station 30.

The following describes the individual worksteps (FIG. 3):

a) First, a basket (19b, for example) is moved from first partial segment 11a along the curved section located at end 14 to second partial segment 11b.

b) Then the row of baskets located in first partial segment 11a is advanced one place to create an empty place behind entrance door 16.

c) The entrance door 16 opens to admit another basket (19a in the example), which is filled with objects to be decontaminated, into the empty place previously created in first partial segment 11a.

d) During loading and unloading, the baskets are advanced one place at loading and unloading station 30.

e) Then basket 19c located at the end of reaction section 11 can be guided through exit door 17 to loading and unloading station 30.

f) The row of baskets located in second partial segment 11b is then advanced one place.

The above steps a) to f) are then repeated. The conveyor system for the baskets is coupled to the SPS control, so that these worksteps are automated.

Baskets 19 located inside reaction chamber 10 are exposed to a hot gas mixture provided by a gas supply and exhaust system (not shown) via feeds 41 (FIGS. 5–7), which generates a lengthwise gas flow and a transverse gas flow within reaction section 11, as described below.

Feeds 41 (shown schematically in FIGS. 5–7) connected to the gas generator (not shown) feed the lengthwise gas flow (FIGS. 2, 3 and 5) in rear end 15 of reaction chamber 10 in both partial segments 11a and 11b. An exhaust blower 42 (FIGS. 2 and 3) is located at front end 14, which generates a vacuum to draw the hot gas mixture away and blow it into the open. A lengthwise gas flow is thus generated in both partial segments 11a and 11b (FIGS. 2, 3 and 5) of reaction section 11, said flow running in the same direction as the conveyor direction of baskets 19 in first partial segment 11a and in the opposite direction in second partial segment 11b. In addition, the vacuum in reaction chamber 11 ensures that when doors 16 and 17 are opened and closed during loading and unloading, no possibly contaminated gases can escape.

Figure 2:
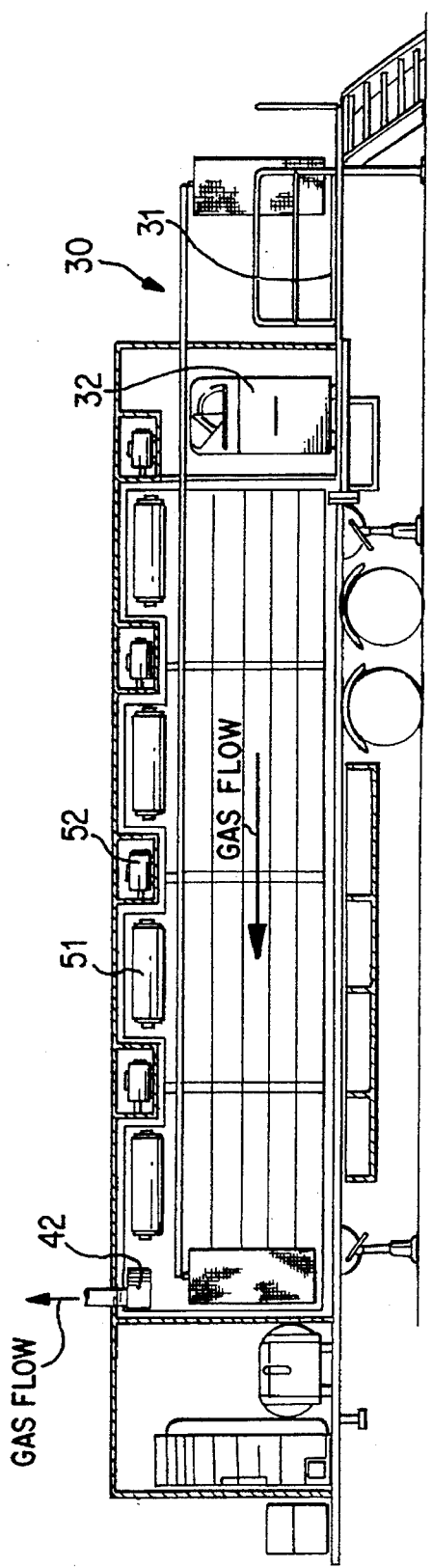
FIG. 2 is a front view of the trailer shown in FIG. 1, in section.

As for transverse gas flow 50 (FIGS. 1 and 4), a plurality of transverse-flow blowers 51 (FIGS. 1, 2, and 4) are mounted on the roof of the reaction chamber, each driven by a diesel unit 52 (FIG. 2). Each transverse-flow blower 51 (FIG. 4) blows the gas mixture through an exhaust screen 53 (FIGS. 1 and 4) located on one of the two side walls of each reaction section. Screen 53 serves as a gas guiding element in order to ventilate baskets 19 as uniformly as possible. The hot gas mixture flows laterally, transversely with respect to the conveying direction, through the baskets and then is drawn off by transverse flow blower 51. Because of the good ventilation of the objects to be decontaminated by the hot gas mixture, rapid heat transfer is achieved and hence rapid destruction of the biological or chemical contaminates. In addition, the transverse gas flow in the circuit results in a high degree of utilization of the hot gas mixture.

Figure 5:
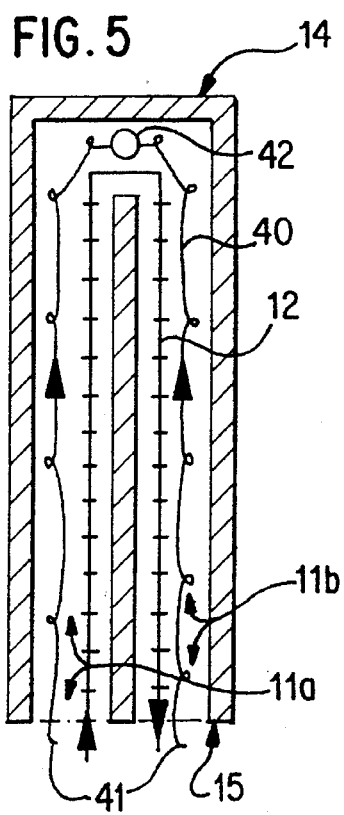
FIG. 5 is a schematic top view of the reaction chamber shown in FIG. 1, in section.
Figure 6:
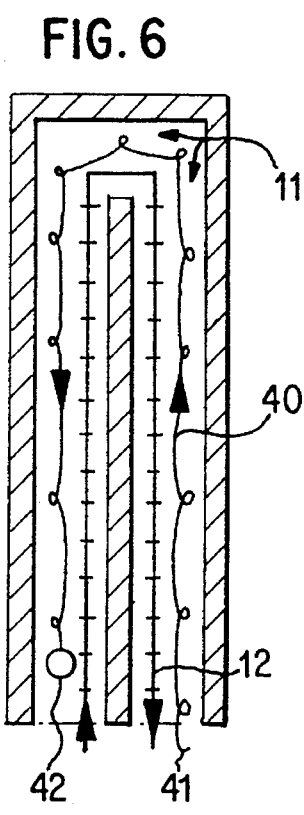
FIGS. 6 and 7 each show an alternative design for the reaction chamber, in a schematic top view and in section.
Figure 7:
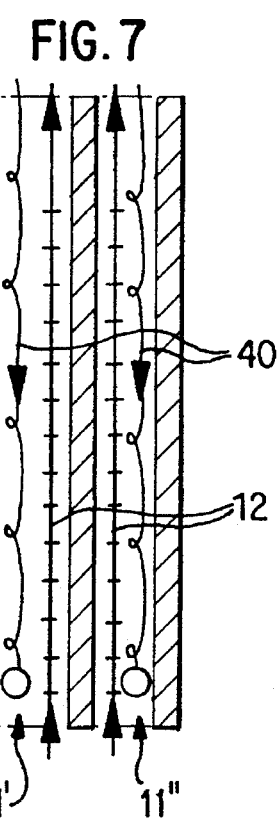

FIGS. 5, 6 and 7 are schematic diagrams showing the relationships between the path of the reaction section within the reaction chamber and the lengthwise gas flow. While FIG. 5 corresponds to the previous embodiment, FIGS. 6 and 7 each show an alternative embodiment. Their versions will be compared with one another in the following.

FIG. 5 represents the embodiment discussed earlier in which:

a) the reaction section consists of two partial segments 11a and 11b located side by side, and sequentially along the path of the conveyor guide rail 18;

b) each partial segment 11a and 11b is provided at the rear end 15 of the reaction chamber with a feed 41 for the hot gas mixture;

c) exhaust blower 42 is mounted on front end 14;

d) because of b) and c) above, in each partial segment 11a and 11b a lengthwise gas flow 40 causes a flow that moves in the same direction as conveyor direction 12 for the baskets in first partial segment 11*a* and in the opposite direction in second partial segment 11*b*.

In contrast to the previous embodiment, the version shown in FIG. 6 shows that the hot gas mixture is supplied only at the back end of reaction section 11, through feed 41;

suction blower 42 is mounted at the beginning of reaction section 11;

lengthwise gas flow 40 extends over nearly all of reaction section 11 (except for a short portion at the entrance door) in a direction 12 opposite to that in which the baskets are conveyed.

A disadvantage of the above embodiment is that:

the temperature of the hot gas mixture decreases as the distance traveled by the gases along reaction section 11 increases, because of heat losses, resulting in a deterioration of decontamination efficiency.

In contrast, FIG. 7 shows that:

two reaction sections 11' and 11" are provided to permit parallel operation;

lengthwise gas flow 40 through the entire reaction sections 11' and 11" is directed counter to direction 12 in which the baskets are conveyed.

In this third design, the baskets must be returned along an additional path to the beginning of reaction sections 11' and 11".

The embodiment of the reaction chamber 10, shown in FIG. 1, is also designed for nuclear decontamination. For this purpose, in a first section of reaction section 11, nozzles for spraying decontamination solution are provided on a spray rack in a conventional manner. In a subsequent section of reaction section 11, spray racks are likewise provided with nozzles for washing off the decontamination solution with a rinsing solution (water for example). In a final section of reaction section 11, blowers are provided for drying with hot air. The decontamination and rinsing solutions are supplied through an external connection. To achieve a high degree of decontamination, each set of clothing and equipment items is distributed between two baskets 19. The operation for nuclear decontamination, like biological and chemical decontamination, is supported by the SPS control system and is therefore automated.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A biological and chemical decontamination chamber comprising:

an elongated, tunnel reaction section which is enclosed along a periphery thereof;

at least one path disposed within said reaction section, which path comprises longitudinal segments that are laterally adjacent to one another and sequentially connected to one another;

a conveyor having a guide rail arranged along said at least one path in said reaction section;

a plurality of gas permeable baskets coupled to and movable along said guide rail for transporting contaminated articles through said reaction section;

an entrance door at a beginning of said reaction section, for entry of baskets into said reaction section along said guide rail;

an exit door at an end of said reaction section for discharging baskets from said reaction section;

at least one gas feed for supplying a mixture of decontaminant gases to said reaction section, said gas feed being situated at a first end of said reaction section;

at least one exhaust blower coupled to said reaction section at a second end thereof, said second end being situated relative to said first end in a direction which is opposite a direction of movement of said baskets in a final segment of said reaction section, and the same as a direction of movement of said baskets in an initial segment thereof;

a plurality of transverse flow blowers situated along a longitudinal axis of said reaction section; and a plurality of gas guiding elements coupled to said transverse flow blowers, for directing flow of said mixture of decontaminant gases in a direction transverse to said longitudinal axis.

2. Decontamination chamber according to claim 1, wherein said reaction chamber is mounted on a transportable chassis.

3. Decontamination chamber according to claim 2, further comprising:

first spray racks located in a first portion of said reaction section, said first spray racks having nozzles for spraying decontamination fluid to rinse nuclear contaminants from contaminated articles;

second spray racks located in a following portion of said reaction section, said second spray racks having nozzles for washing off decontamination fluid with a rinsing solution; and blowers for drying with hot air provided in a last segment of said reaction section.

4. Decontamination chamber according to claim 1, wherein said transverse flow blowers are mounted at a top portion of said reaction chamber.

5. Decontamination chamber according to claim 1, wherein the gas guiding elements comprise screens which direct the hot gas mixture.

6. Decontamination chamber according to claim 5, wherein said screens are arranged along at least one side of said reaction section, and wherein during operation, said transverse flow blowers blow said mixture of decontaminant gases through said screens.

7. Decontamination chamber according to claim 5, further comprising:

first spray racks located in a first portion of said reaction section, said first spray racks having nozzles for spraying decontamination fluid to rinse nuclear contaminates from contaminated articles;

second spray racks located in a following portion of said reaction section, said second spray racks having nozzles for washing off decontaminated fluid with a rinsing solution; and blowers for drying with hot air provided in a last segment of said reaction section.

8. Decontamination chamber according to claim 1, wherein:

said longitudinal segments are connected at at least said second end of said reaction section;

a beginning of said initial segment relative to movement of said baskets, and an end of said final segment relative to movement of said baskets, are situated at said first end of said reaction section; and said entrance door is situated adjacent said beginning of said initial segment and said exit door is situated adjacent said end of said final segment.

9. Decontamination chamber according to claim 1, further comprising:

first spray racks located in a first portion of said reaction section, said first spray racks having nozzles for spraying decontamination fluid to rinse nuclear contaminants from contaminated articles;

second spray racks located in a following portion of said reaction section, said second spray racks having nozzles for washing off decontamination fluid with a rinsing solution; and blowers for drying with hot air provided in a last segment of said reaction section.

10. Decontamination chamber according to claim 1, wherein said mixture of decontaminant gases comprises at least hot air and steam.

11. A biological and chemical decontamination chamber comprising:

an elongated, tunnel reaction section which is enclosed along a periphery thereof, said reaction section comprising at least one path disposed within said reaction section, which path comprises longitudinal segments that are laterally adjacent to one another and sequentially connected to one another;

a conveyor having a guide rail arranged along said at least one path in said reaction section;

a plurality of gas permeable baskets coupled to and movable along said guide rail for transporting contaminated articles through said reaction section;

at least one gas feed for supplying a mixture of decontaminant gases to said reaction section, said gas feed being situated at a first end of said reaction section;

at least one exhaust blower coupled to said reaction section at a second end thereof, said second end being situated relative to said first end in a direction which is opposite a direction of movement of said baskets in a final segment of said reaction section, and the same as a direction of movement of said baskets in an initial segment thereof.

* * * * *